US006281973B1

(12) United States Patent
Trainer

(10) Patent No.: US 6,281,973 B1
(45) Date of Patent: Aug. 28, 2001

(54) OPTICAL DETECTION SYSTEM AND METHOD FOR DETERMINING PARTICLE SIZE DISTRIBUTION IN AN OSCILLATING FLOW FIELD

(75) Inventor: Michael N. Trainer, Telford, PA (US)

(73) Assignee: Microtrac, Inc., Montgomeryville, PA (US)

(*) Notice: Subject to any disclaimer, the term of this patent is extended or adjusted under 35 U.S.C. 154(b) by 0 days.

(21) Appl. No.: 09/406,944

(22) Filed: Sep. 28, 1999

(51) Int. Cl.[7] .................................................. G01N 21/00

(52) U.S. Cl. .......................................... 356/342; 356/337

(58) Field of Search .................................... 356/336, 337, 356/338, 342, 308, 285; 250/574, 575; 73/865.5

(56) References Cited

U.S. PATENT DOCUMENTS

| | | | |
|---|---|---|---|
| 3,208,286 | * | 9/1965 | Richard ................................ 73/865.5 |
| 4,906,092 | * | 3/1990 | O'Meara ............................. 356/28.5 |
| 5,094,532 | * | 3/1992 | Trainer et al. ....................... 356/336 |

* cited by examiner

Primary Examiner—Hoa Q. Pham
Assistant Examiner—Sang H. Nguyen
(74) Attorney, Agent, or Firm—Wood, Herron & Evans, LLP

(57) ABSTRACT

An optical detection system and method is disclosed comprising a first light guide for conveying light energy from a light source to a first light guide face end that is immersed in a dispersant medium. A first portion of the light energy exits the face end to irradiate particles contained in the dispersant medium and a second portion of the light energy is reflected by the face end back into the first light guide. A frequency transducer mounted to the first light guide receives at least one specific frequency from a range of frequencies generated by a frequency oscillator and oscillates the first light guide face end at the applied specific frequency. The transducer oscillations are further coupled into the dispersant medium, causing the dispersant medium and the particles contained therein to oscillate at the oscillation frequency of the first light guide face end. The light energy scattered by the oscillating particles is captured by the first light guide face end and is mixed within the first light guide with the reflected light energy, producing an optical Doppler beat signal for the applied specific frequency. A second light guide, optically connected to the first light guide, conveys the optical Doppler beat signal to a light detection device that produces an output signal representative of the optical Doppler beat signal. A mixer circuit receives the specific frequency signal from the frequency oscillator and the output signal from the detection device and produces a plurality of derived harmonics for the input specific frequency signal. The mixer circuit further generates frequency components for the input Doppler beat signal producing a total power value signal for each derived harmonic of the frequency. The total power value signals are applied to a signal processing system that calculates a particle motion amplitude signal for each applied specific frequency. The particle motion amplitude signal is used to determine the percentage of the total particles which are following the oscillations of the dispersant fluid at the applied specific frequency.

9 Claims, 5 Drawing Sheets

OPTICAL DETECTION SYSTEM AND METHOD FOR DETERMINING PARTICLE SIZE DISTRIBUTION IN AN OSCILLATING FLOW FIELD

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates generally to the field of determining particle size distribution and more specifically to an optical detection system and method for the measurement of particle size distribution in a flow field that is oscillated at various frequencies.

2. Discussion of the Related Art

The measurement of particle size distribution finds use in the process industries in the manufacture of pharmaceuticals, chemicals, abrasives, ceramics, pigments and the like, where the particle size affects the quality of the manufactured product.

A number of methods presently exist for determining the size distribution of particulate material for particles in the approximate size range of 0.1 to 1000 microns in diameter. The conventional method of measurement at high concentration is dynamic light scattering, as taught by U.S. Pat. No. 5,094,532 to Trainer et al., patented Mar. 10, 1992. This patent discloses a fiber optic Doppler anemometer and method that directs a beam of light into a scattering medium that contains particles in Brownian motion. The frequency of the scattered light is compared to non-scattered light emitted from the scattering medium and results in the generation of a first signal having a magnitude that is indicative of the difference in frequency between the scattered light and the non-scattered light. A second signal is generated having a magnitude that varies with frequency on a linear scale. The frequency scale of the second signal is then translated into a logarithmic scale and deconvolved to determine the size and distribution of moving particles within the scattering medium. The translation and deconvolving requires translation of analog signals to digital signals and subsequent processing by a central processor and a vector signal processor using fast Fourier transform techniques (FFT). In order to solve for a known particle size distribution of over 80 particle diameters the method just described must sample over 80 frequencies. Even though this method provides an accurate measurement of particle size distribution, it does require a long time period (usually greater than two minutes) to process all of the sample frequencies, due primarily to the stochastic nature of Brownian motion. This technique is best suited for use in a laboratory with samples that have been extracted from a process and properly prepared for measurement analysis. Additionally, this method is strongly dependent upon dispersant viscosity and temperature and the use of non-flowing sample delivery systems. Although this technique provides accurate results for particles having diameters less than 1 micron, it exhibits poor size and volume accuracy for particles above 1 micron.

Another recognized technique and method for measuring the size distribution of very small particles is static light scattering, or angular light scattering. In this method, a collimated monochromatic light beam irradiates an ensemble of particles that flow perpendicularly through the collimated light beam. Light scattered from the particles emerges from the interaction over a range of angles from the axis of the collimated beam. The scattered light is collected by a lens placed in the path of the scattered light. The scattered light patterns focused in the focal plane of the lens are typically measured by an array of photodetectors placed in the focal plane. The angular extent of the scatter pattern is determined by the size of the particles. The smaller the particle, the wider the angular extent of the scatter; the larger the particle, the narrower the angular extent of the scatter.

One such method is taught by U.S. Pat. No. 5,416,580 to Trainer, patented on May 16, 1998, which uses multiple light beams to irradiate the particles. This method has demonstrated excellent measurement results for particles in the 0.1 to 3000 micron range in flowing sample systems, without temperature or viscosity dependency. Unlike the dynamic scattering techniques, measurements can be made in less than five seconds with repeatability superior to that of the dynamic light scattering. However, in order to produce good measurement accuracy for a process sample at a high concentration, for example 10% by volume, the process sample must be properly diluted with a dispersant medium to minimize the particle concentration.

Each of the above described techniques is limited to a certain range of particle size, concentration and shape. Particles of many shapes are encountered in the aforementioned industrial processes. In certain applications hydrodynamic particle size measurement techniques present a better correlation to the product quality than the optical particle size measuring techniques for irregularly shaped particles. A particularly difficult region is between 0.5 to 1 microns, where both static and dynamic scattering can present somewhat of a less-than-accurate measurement of particle size distribution. Hydrodynamic particle size measurement techniques include a basic concept of detecting a particle's motion or oscillations in a fluid dispersant caused by a vibrating surface or an ultrasonic wave. Depending on the oscillating frequency applied to the dispersant fluid, the particles will closely follow the oscillation of the dispersant fluid.

BRIEF SUMMARY OF THE INVENTION

It is, therefore, an object of the present invention to provide an optical detection system and method that employs an oscillating flow field used in the accurate measurement of particles suspended within a dispersant medium.

In accordance to the object of the present invention there is provided an optical detection system and method comprising a light source for producing light energy and a first light guide for conveying the light energy from the light source to a first light guide face end that is immersed in the dispersant medium. A first portion of the light energy exits the face end to irradiate the particles contained in the dispersant medium and a second portion of the light energy is reflected from the face end back into the first light guide.

The optical system of the present invention further includes a frequency oscillator that produces at least one signal representing a specific frequency within a frequency range. A frequency transducer mounted to the first light guide receives the frequency oscillator signal and oscillates the first light guide face end at the applied specific frequency. The transducer oscillations are further coupled into the dispersant medium, causing the dispersant medium and the particles contained therein to oscillate at the oscillation frequency of the first light guide face end. The light energy scattered by the oscillating particles is captured by the first light guide face end and is mixed within the first light guide with the reflected light energy, producing an optical Doppler beat signal for the applied specific frequency. A second light guide, optically connected to the first light guide, conveys the optical Doppler beat signal to a light detection device. The light detection device produces an output signal representative of the optical Doppler beat signal.

A mixer circuit receives the specific frequency signal from the frequency oscillator and the output signal from the detection device and is arranged to produce and track the center of a plurality of derived harmonics for the input-specific frequency signal. The mixer circuit further generates frequency components for the input Doppler beat signal for each derived harmonic that is used for producing a total power value signal for each derived harmonic of the frequency.

The total power value signals are applied to a signal processing system that calculates a particle motion amplitude signal for each applied specific frequency. The particle motion amplitude signal is used to determine the percentage of the total particles which are following the oscillations of the dispersant fluid at the applied specific frequency. Using a theoretical model of particle motion in an oscillating dispersant medium, this percentage is used to determine the particle size distribution measurement.

BRIEF DESCRIPTION OF THE DRAWINGS

Other objects, features, and advantages of the present invention will be apparent from the following description of a preferred embodiment thereof, taken in conjunction with the sheets of drawings, in which.

DETAILED DESCRIPTION OF THE INVENTION

The degree to which particles will follow dispersant motion depends upon ultrasonic wave frequency, particle size, particle density and dispersant density and viscosity. Particles will accurately follow the ultrasonic motion of the dispersant at low frequencies. However, at certain higher frequencies the relative amplitude and phase between particles and dispersant motion will change. The phenomenon of particle motion relative to dispersant motion is graphically shown in FIG. 1 where the particle-to-dispersant density ratio is 1.2 and dispersant viscosity is 1 centipoise. The data represent particle diameters between 0.25 and 32 microns, over a liquid or dispersant frequency range from 10 Hz to 100 Mhz. Each particle size represented has a frequency range transition region that below this region the particles follow closely the oscillation of the dispersant and above this region the particles' motion is attenuated, relative to the motion of the dispersant. For larger particles, motion will be attenuated by 12% (88% of the fluid motion) at high fluid oscillation frequencies. For smaller density ratios such as 1.05, such as found for polystyrene in water, the motion difference between the particles and fluid is only 3% of the fluid motion. When using heterodyne detection, or self beating techniques, to detect this motion, the spectrum of the scattered light will show peaks at harmonics of the fluid oscillation frequency. The amplitude of these spectral peaks is usually described by Bessel functions and will be indicative of the particle motion amplitude. As the frequency is increased, more particles will join the attenuated-motion particle population (12% attenuation in the above example). The change in this population size for each increment of frequency change will determine how many particles are in that corresponding size range. As can be seen in FIG. 1, the added number of particles which show motion attenuation in the frequency range between 100 kHz and 400 kHz represents the particles in approximately the 2 to 4 micron size region. The spectrum can be used to determine the cumulative size distribution, which can then be differentiated to create a differential volume (or number) relative to size distribution. For low particle/fluid density ratios, such as the aforementioned 1.05 ratio of polystyrene in water, the determination of the motion-attenuated particles becomes difficult when measuring a 3% change in particle velocity. Direct measurement of the particle velocity relative to the fluid would be more accurate than measuring the absolute particle motion.

In homodyne detection, the scattered light from the particles in motion mixes and interferes with the scattered light from the particles with attenuated-motion to create the scattering spectrum. At the lowest dispersant oscillation frequencies, all of the particles in suspension move or oscillate and no homodyne signal is detected. However, as the frequency and the number of attenuated-motion particles increase, the interference between the scattered light from these two populations will produce Doppler beat frequencies in the detector current of an optical detector device used to detect the spectrum. Since the attenuated-motion population increases at the expense of the unattenuated population, the interference amplitude has a peak when both populations are of equal size.

If X is the attenuated-motion particle fraction of the total population, then the interference signal power depends upon the attenuated-motion particle population fraction in accordance to the function:

$$(1-X)*X$$

The homodyne interference signal in relation to an attenuated-motion particle population is shown in FIG. 2. As can be seen, between the attenuated-motion population fractions of 40% to 60%, the homodyne interference amplitude has a low sensitivity to the magnitude of the attenuated-motion population and is thereby prone to particle size distribution errors. The present invention eliminates this sensitivity by using heterodyne detection by means of a local oscillator that moves with the oscillations of the dispersant fluid. The local oscillator strength then will be constant at all attenuated population levels over the entire range. This fluid tracking local oscillator is produced by creating a partial optical reflector on the same vibrating surface which is driving the particles.

The present invention contemplates vibrating the optical probe tip of a fiber optic device such as the optical velocimeter taught by U.S. Pat. No. 5,094,526, to Freud et al., and now assigned to Honeywell Inc. In causing the tip of the optical probe to vibrate, only particles which do not follow the motion of the fiber tip would contribute to the heterodyne motion. The only difference between the dispersant fluid and the motion of the fiber tip is due to the compressibility of the dispersant fluid, which could be accounted for. Such a fluid tracking local oscillator would provide a true fluid/particle motion measurement that is sensitive to particle sizes over a large particle size measurement range.

Therefore, the system of the present invention is comprised of a fiber optic probe that includes an ultrasonic transducer that causes the probe tip and the dispersant fluid within a particle sample to vibrate in accordance to selected frequencies. The system further includes an electronic mixer that receives a Doppler beat signal output by the probe 10 and automatically tracks the harmonics of the fluid vibration frequency at each ultrasonic frequency applied. The electronic mixer generates signals used by a digital computing device for calculating the percentage of the total particles of a particle ensemble that are in motion at a particular frequency.

Figure 1:
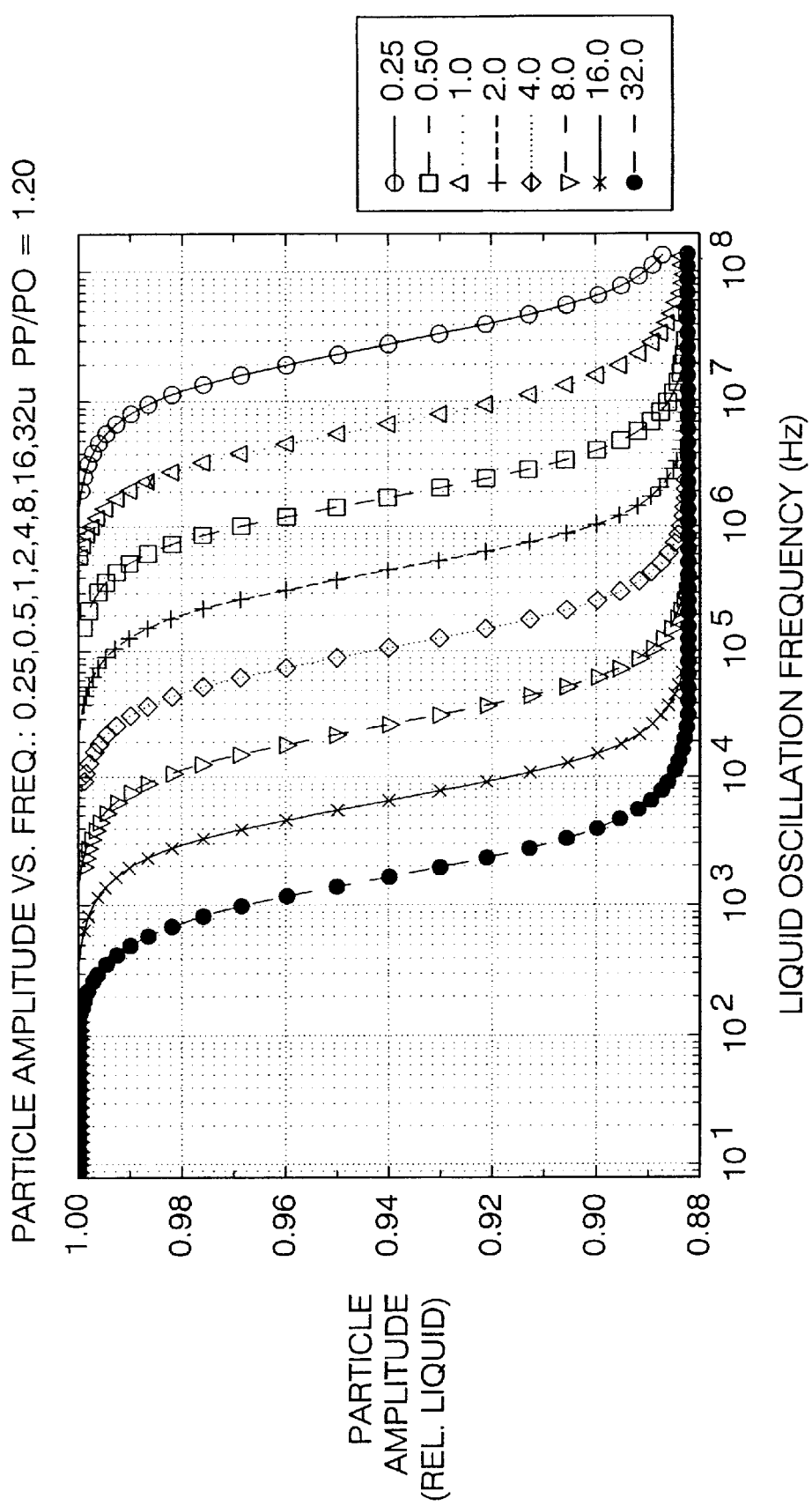
FIG. 1 illustrates, in the form of a graph plot, the particle amplitude of various particle sizes at various dispersant oscillation frequencies.
Figure 2:
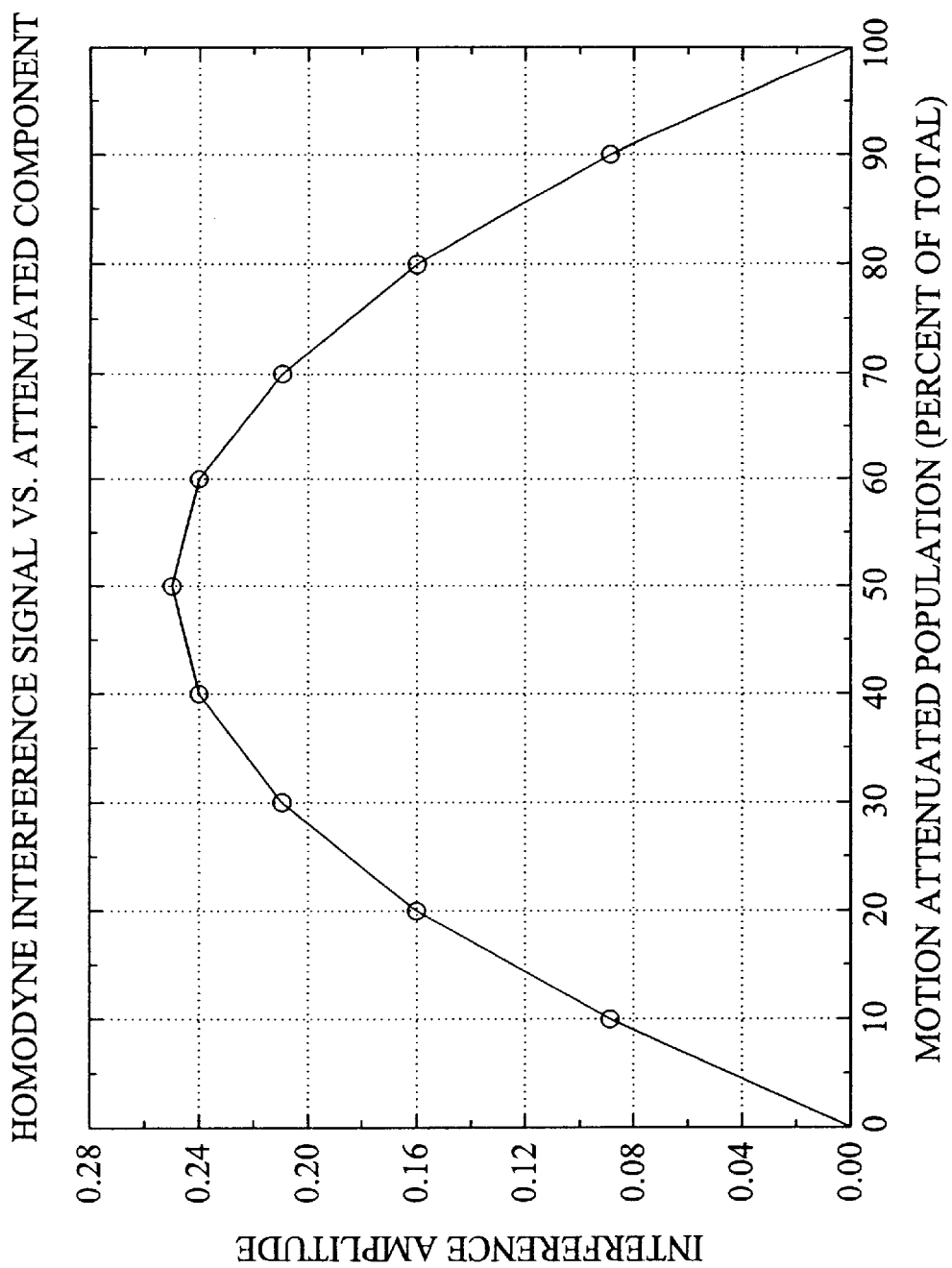
FIG. 2 illustrates, in the form of a graph plot, the homodyne interference signal in relation to an attenuated-motion particle population.
Figure 3:
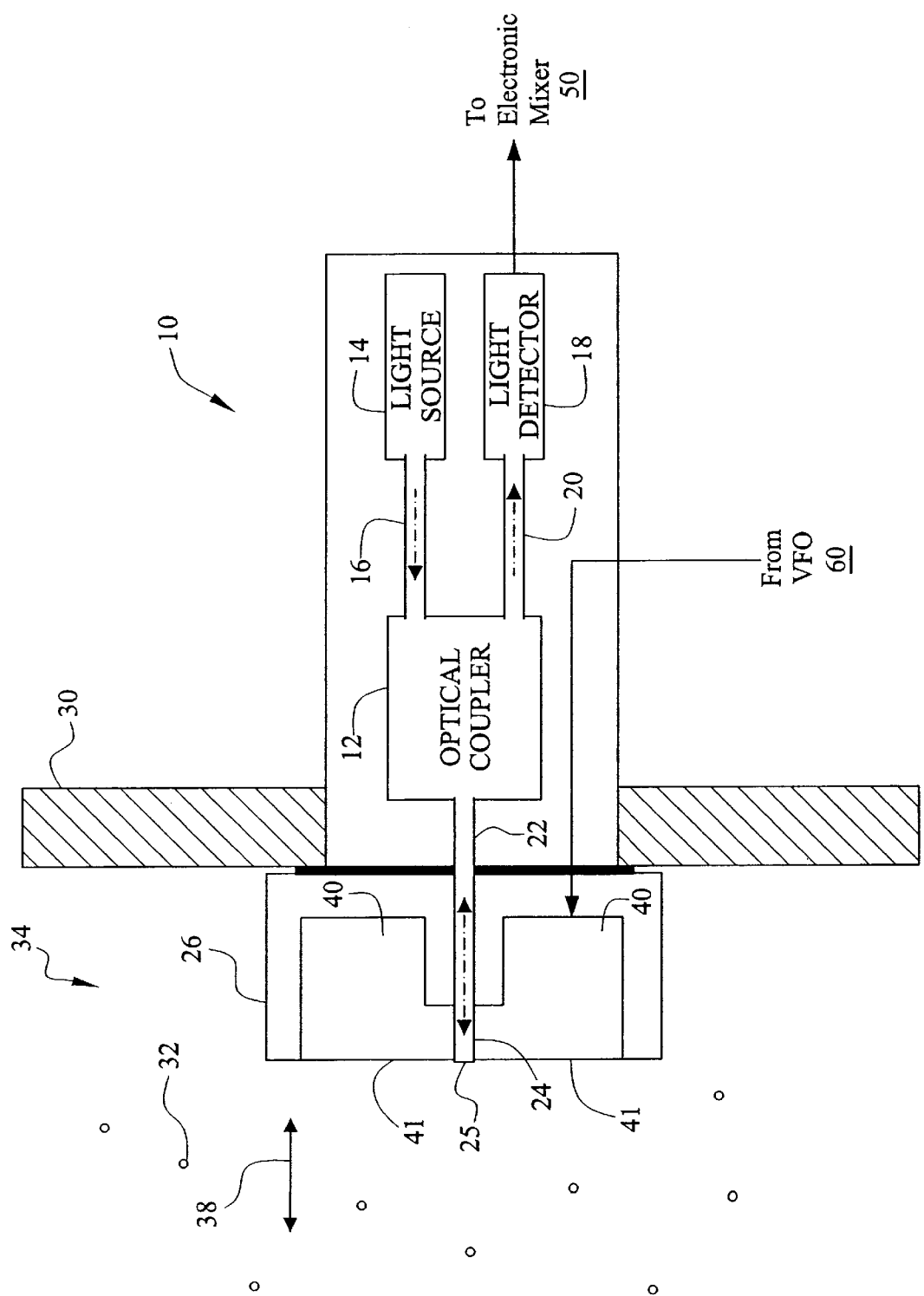
FIG. 3 is a schematic diagram of the fiber optic probe in accordance to the present invention.

Turning now to FIG. 3, a schematic diagram of a fiber optic probe 10 used in the present invention is shown. The probe 10 shown represents one possible construction of such an optical device than can be used to advantage in accordance to the teachings of the present invention. For example, the aforementioned velocimeter taught by U.S. Pat. No. 5,094,526 can be modified in accordance to the present invention to cause the fiber tip of the velocimeter to vibrate at various frequencies in order to practice the advantages of the present invention.

The probe 10 illustrated consists of a fiber optic coupler 12, a source of laser light 14 optically connected to the coupler 12 via a source light fiber 16 and a light detector 18 optically connected to the coupler 12 via a detector fiber 20. An exit fiber 22 extends from the coupler 12 to a fiber tip 24 located within a head end 26 of probe 10. The probe 10 is attached to a wall 30 of a sample cell 34. The head end 26 is substantially submerged into sample cell 34 that contains particulate matter 32 suspended in a dispersant fluid, such as water. The particular dispersant fluid may be selected from a wide range of media as long as it is inert with respect to the particulate matter 32 suspended therein. Even though head end 26 is described in this embodiment as immersed into a sampling cell 34 that is isolated from a manufacturing process, it will be well understood by those skilled in the art that the cell 34 could be part of an apparatus which extracts representative samples of the manufactured product withdrawn from a conduit transporting the product from one stage of the manufacturing process to another. The prepared sample can be automatically delivered to the cell 34 or delivered on a demand basis.

The head end 26 also includes an ultrasonic transducer 40 that is mounted about the tip end 24 in any convenient manner presently known. The ultrasonic transducer 40 is electrically connected to a variable frequency oscillator (VFO) and operated to vibrate at various ultrasonic frequencies. Surface 41 of ultrasonic transducer 40 and a face 25 of the fiber tip 24 form a reflecting surface that couples the vibrations imparted by the ultrasonic transducer 40 into the dispersant fluid contained in sample cell 34. The vibrations are conducted into the dispersant fluid perpendicular to face 25 in the direction illustrated by arrow 38.

Figure 4:
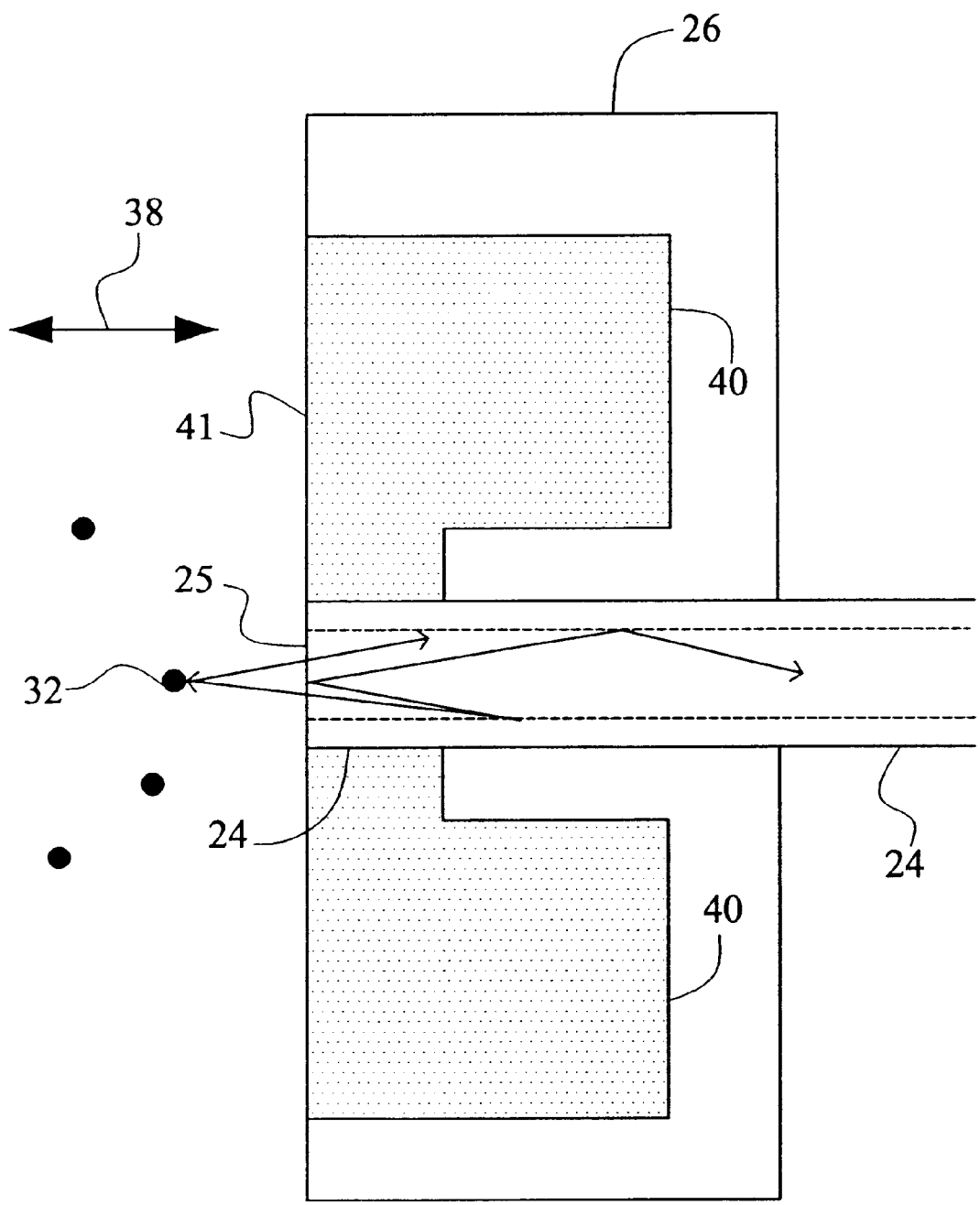
FIG. 4 is a schematic diagram of the head end of the fiber optic probe illustrated in FIG. 3 in accordance to the present invention.

With reference to FIG. 3 and FIG. 4 an explanation of the operation of fiber optic probe 10 of the present invention will now be made. Light energy from the laser light source 14 is optically coupled into the source light fiber 16 and to the coupler 12. The source light is then directed to the exit fiber 22 where it travels to fiber tip 24, exiting at face 25 and propagated into the dispersant fluid and the particles 32 suspended therein. A portion of the light energy reaching fiber tip 24, however, is back-reflected by the face 25 back into the fiber tip 24, producing an optical heterodyne local oscillator signal. The light energy not back-reflected passes out of face 25 into the dispersant fluid as a scattering source. The light energy passing into the sample is scattered by the particles 32 suspended therein. The scattered light energy re-enters the fiber tip 24 at face 25 and is conveyed along with the local oscillator signals through the exit fiber 22, the coupler 12 and detector fiber 20 and mixed at the light detector 18 to produce a Doppler beat signal. The Doppler beat signal is converted by the light detector 18 into an electrical signal for further processing by the electronic mixer 50 of the present invention.

Since the dispersant fluid vibrates along with the reflecting surface comprised of surface 41 and face 24, the detected Doppler beat signal will be representative of only the particles that are moving relative to the reflecting surface and that of the dispersant fluid. These particles would represent the particle population with attenuated-motion, which no longer follow the motion of the dispersant fluid. By measuring the number of particles with attenuated-motion at different fluid oscillation frequencies, the cumulative size distribution is created. The differential distribution is the derivative of this cumulative distribution.

The range of light energy scattered by a particle oscillating relative to the local oscillator, will contain a sinusoidal phase component that is relative to the phase of the local oscillator. The heterodyne detector current ($I_{HET}$) of the light detector 18 is proportional to the product of the square root of the local oscillator and the square root of the intensities of the scattered light energy detected and the cosine of their phase differences. The phase difference includes the particle motion within a certain fluid oscillation frequency ($\omega_O$), and a static phase ($\theta$) that defines the random position of the particles without motion. This static phase will take on random values for each particle in a particle ensemble. Therefore, in order to retrieve the distribution of particle motion amplitude (A), over a particle ensemble, the power (mean square value) of the detector current must be measured in order to eliminate the effect of the random static phase of the individual particles. This measurement of detector current can be derived using the following formula:

$$I_{HET} = (I_O * I_S)^{1/2} * \cos(\theta + k * A * \cos(\omega_o t + \phi))$$

where $k = 2\pi/\lambda$ $I_O$=the local oscillator intensity $I_S$=the scattered light intensity $\theta$=the static phase from the initial position of the particle $\lambda$=the light wavelength $\omega_o$=the ultrasonic fluid oscillation frequency $\phi$=fluid motion phase offset.

The power spectrum, P(ω), of the detector current (at frequency ω) will contain line spectra at harmonics of the fluid oscillation frequencies, in accordance to:

$$P(\omega)=\Sigma F_n(D(A))*\delta(\omega-n\omega_o)$$

where $\delta(\omega)$=Dirac delta function n=0,1,2, . . .

$F_n$=combinations of Bessel functions.

With the power spectrum of the detector current calculated, the distribution of particle motion amplitude D(A), is determined by the solution of a series of linear equations:

$$D(A_i)=\Sigma M_{ij}*F_j$$

where $D(A_i)$=the percent of particles with motion amplitude $A_I$ $F_j$=the value of the total power in the jth. spectral line $M_{ij}$=the model matrix for given measurement conditions.

The values of $F_j$ can be measured with a spectrum analyzer or narrowband analog filters. However, the centers of the analog filters must track the harmonics of the fluid vibration frequency at each ultrasonic frequency applied by the ultrasonic transducer 40 to the dispersant fluid.

Figure 5:
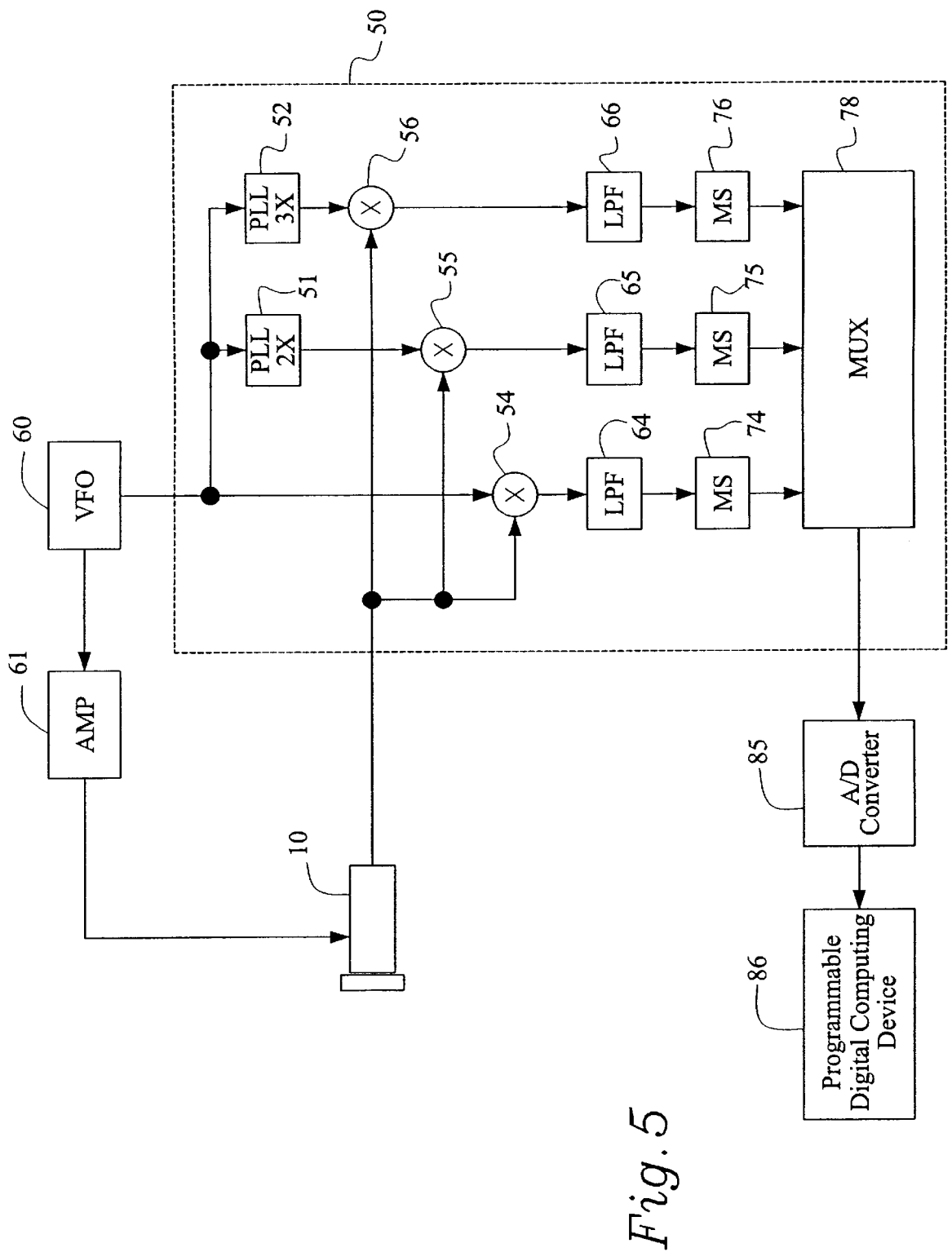
FIG. 5 is a schematic diagram of the optical detection system used for the measurement of particle size distribution in an oscillating flow field in accordance to the present invention.

Turning now to FIG. 5, a schematic diagram of the electronic mixer 50 of the present invention is shown. The electronic mixer is electrically connected to a variable frequency oscillator (VFO) 60, the fiber optic probe 10 and to an A/D converter 85. The VFO 60 drives the ultrasonic transducer 40 of the fiber optic probe 10 through an amplifier 61 from a few Hertz to the Megahertz range. The VFO 60 signal frequency is also input to mixer 50 and applied to a set of included phase lock loop circuits (PLL). The input VFO 60 signal frequency is multiplied up by PLL circuits 51, 52 to generate individual sinusoids for all appropriate harmonics of the applied ultrasonic transducer frequencies. For matters of clarity, only the first two harmonics 2× and 3× are shown in FIG. 5. The output of PLL 51, 52 is applied to an associated analog multiplier 55, 56 respectively. The VFO 60 signal frequency is directly applied to multiplier 54. Each multiplier 54, 55 and 56 is further electrically connected to the optical detector 18 of fiber optic probe 10 and each receive the electrical Doppler beat signal representing the particle population contained within the sample having attenuated motion. The multipliers 54, 55 and 56 generate sum and difference frequency components from the input Doppler beat signals for each harmonic generated. An individual analog electronic low pass filter (LPF) circuit 64, 65 and 66 is associated with and connected to an associated multiplier. Each LPF 64, 65 and 66 is arranged to select the difference frequency component that shifts the spectra down to baseband. The output of each LPF circuit is next applied to an associated analog mean square circuit (MS) 74, 75 and 76 that measures the total power within the bandwidth of the associated LPF. Each signal derived from the individual MS circuits 74, 75 and 76 is next applied to a signal multiplexer (MUX) 78 that sequentially selects the power value in the LPF bandpass about each harmonic. Each power value selected by MUX 78 is converted to digital data by the A/D converter 85 before being applied to a programmable digital computing device 86. Each digitized power value represents the $F_j$ value used in the linear equation above to solve for the distribution of particle motion amplitude D(A). The digital computing device 86 contains the programming for effecting the aforementioned calculations for solving the distribution of particle motion amplitude D(A). A different D(A) vector is derived for each ultrasonic frequency applied to the sample in order to determine the percentage of the total particles which are following the dispersant fluid at each applied frequency and used to determine, based on a theoretical model of particle motion in an oscillating dispersant, the particle size distribution measurement.

The present invention has been described with particular reference to the preferred embodiments thereof. It will be obvious that various changes and modifications can be made therein without departing from the spirit and scope of the invention as defined in the appended claims.

What is claimed is:

1. An optical detection system used in determining the size distribution of particles contained in a dispersant medium, said optical detection system comprising:

a light source for producing light energy;

a first light guide for conveying said light energy from said light source to a first light guide face end, said light guide face end immersed in said dispersant medium, whereby a first portion of said light energy exits said face end to irradiate the particles contained in said dispersant medium and a second portion of said light energy is reflected from said face end back into said first light guide;

a frequency oscillator for producing at least one signal representing a specific frequency within a frequency range;

a frequency transducer coupled with said first light guide and connected to said frequency oscillator, said frequency transducer operable to receive said frequency oscillator signal and to oscillate said first light guide face end and said dispersant medium at the specific frequency, said particles contained in said dispersant medium oscillating at the oscillation frequency of said first light guide face end;

said first light guide face end capturing the light energy scattered by the particles that are oscillating at the oscillation frequency of said first light guide face end, said captured light energy and said reflected light energy mixing within the first light guide and producing an optical Doppler beat signal for the applied specific frequency; and a second light guide optically coupled to said first light guide for conveying said optical Doppler beat signal to a light detection device, said light detection device producing an output signal representative of said optical Doppler beat signal.

2. The optical detection system as claimed in claim 1 wherein said optical detection system comprises a mixer circuit arranged to receive said specific frequency signal from said frequency oscillator and said output signal from said detection device, said mixer circuit producing and tracking the center of a plurality of derived harmonics of the specific frequency signal and generating frequency components for the input Doppler beat signal for each derived harmonic, thereby producing a total power value signal for each derived harmonic, the power value signal being used in determining the particle population contained in the dispersant medium that is oscillating at the applied specific frequency for determining the particle size distribution.

3. The optical detection system as claimed in claim 2 wherein said frequency oscillator produces a plurality of output signals, each output signal representing a specific frequency within a frequency range, the system further operable wherein each output signal is sequentially applied to said frequency transducer, and an optical Doppler beat signal is produced for each applied specific frequency, said mixer circuit producing and tracking the center of a plurality of derived harmonics for each of the plurality of specific frequency signals, generating frequency components for each of the plurality of input Doppler beat signals for each derived harmonic, thereby producing a total power value signal for each derived harmonic, the power value signal being used in determining the particle population contained in the dispersant medium that is oscillating at each applied specific frequency for determining the particle size distribution.

4. The optical detection system as claimed in claim 2 wherein said mixer circuit further comprises:
   at least one phase locked loop circuit that receives said specific frequency signal from said frequency oscillator for generating an individual sinusoid signal representing a specific harmonic of the applied specific frequency;
   a first analog multiplier circuit receiving said specific frequency signal from said frequency oscillator and said Doppler beat signal from said light detection device for generating sum and difference signals for the input frequency signal;
   at least a second multiplier circuit receiving said sinusoid signal from said phase locked loop circuit and said Doppler beat signal from said light detection device for generating sum and difference signals for the harmonic generated;
   a first low pass filter coupled to said first analog multiplier circuit and a second low pass filter coupled to said second multiplier circuit, each of said first and second low pass filters receiving a respective sum and difference signal from the associated first and second multiplier circuits and each of said first and second low pass filters generating a signal representing the difference frequency component that shifts the frequency down to a baseband signal;
   a first mean square circuit connected to said first low pass filter and a second mean square circuit connected to said second low pass filter, each of said first and second mean square circuits receiving a respective signal from the associated first and second low pass filters and each of said first and second mean square circuits measuring the total power in the low pass filter bandwidth and generating said total power value signal;
   a multiplexer connected to said first and said second mean square circuits receiving each total power value signal and sequentially selecting each total power value signal received for output from said mixer circuit.

5. The optical detection system as claimed in claim 4 wherein said optical detection system further includes a signal processing system and said signal processing system receives each total power value signal from said multiplexer, said signal processing system calculating a particle motion amplitude signal for each applied specific frequency which are used in determining the percentage of the total particles that are oscillating at each applied specific frequency within said frequency range for determining the particle size distribution.

6. The optical detection system as claimed in claim 5 wherein said signal processing system calculates the particle motion amplitude signal for each applied frequency by the solution of a series of linear equations in accordance to:

$$D(A_i) = \Sigma M_{ij} * F_j$$

where
   $D(A_i)$=the percent of particles with motion amplitude $A_I$
   $F_j$=the value of the total power value in the jth. spectral line
   $M_{ij}$=is the model matrix for given measurement conditions.

7. An optical detection system used in determining the size distribution of particles contained in a dispersant medium, said optical detection system comprising:
   a light source for producing light energy;
   first means for conveying said light energy from said light source to an optic end surface, said optic end surface immersed in said dispersant medium whereby a first portion of said light energy exits said optic end surface, irradiating the particles contained in said dispersant medium, and a second portion of said light energy is reflected by said optic end surface;
   means for producing at least one oscillation signal representing a specific frequency within a frequency range;
   means for oscillating said optic end surface coupled to receive the specific frequency signal and oscillate said optic end surface and said dispersant medium at the specific frequency, said particles contained in said dispersant medium oscillating at the oscillation frequency of said optic end surface;
   said optic end surface capturing the light energy scattered by the particles oscillating at the oscillation frequency of said optic end surface, said captured light energy and said reflected light energy mixing in said first means for conveying light energy and producing an optical Doppler beat signal for the applied specific frequency; and
   second means coupled to said first means for conveying said optical Doppler beat signal to a detection device said detection device producing an electrical Doppler beat signal;
   means for receiving said specific frequency signal and said electrical Doppler beat signal and operable to derive and track the center of a plurality of harmonics of the specific frequency signal and generating frequency components for the input Doppler beat signal for each derived harmonic, thereby producing a total power value signal for each derived harmonic of the applied specific frequency; and
   processing means receiving each total power value signal and using each total power value signal and calculating a particle motion amplitude signal for each applied specific frequency, said particle motion amplitude signal being used in determining the percentage of the total particles that are oscillating at each applied specific frequency within said frequency range for determining the particle size distribution.

8. The optical detection system as claimed in claim 7 wherein said processing means is a signal processing system that calculates said particle motion amplitude signal by the solution of a series of linear equations in accordance to:

$$D(A_i) = \Sigma M_{ij} * F_j$$

where
   $D(A_i)$=the percent of particles with motion amplitude $A_I$
   $F_j$=the value of the total power value in the jth. spectral line
   $M_{ij}$=is the model matrix for given measurement conditions.

9. A method for determining the size distribution of particles contained in a dispersant medium, said method comprising the steps of:

conveying light energy from a source of light energy to an end optic submersed in said dispersant medium for irradiating the particles contained in said dispersant medium with said light energy;

oscillating said end optic in at least one frequency within a frequency range, thereby oscillating said dispersant medium and said particles contained therein at the frequency of oscillation of said end optic;

capturing the light energy scattered by the oscillating particles via the end optic;

developing an optical Doppler beat signal with the capture light energy and reflected light energy produced at the end optic;

conveying the optical Doppler beat signal to a detection device, said detection device converting said optical Doppler beat signal to an electrical Doppler beat signal;

producing and tracking the center of a plurality of derived harmonics of the oscillation frequency and generating frequency components for the electrical Doppler beat signal for each derived harmonic, thereby producing a total power value signal for each derived harmonic; and calculating a particle motion amplitude signal using the total power value signals and using the amplitude signal to determine the percentage of the total particles that are oscillating at said applied specific frequency.

* * * * *